(12) United States Patent
Buffa et al.

(10) Patent No.: US 11,427,652 B2
(45) Date of Patent: *Aug. 30, 2022

(54) CHLORINATED DERIVATIVE OF HYALURONIC ACID, METHOD OF PREPARATION THEREOF, A COMPOSITION CONTAINING THE DERIVATIVE, AND USE THEREOF

(71) Applicant: CONTIPRO A.S., Dolni Dobrouc (CZ)

(72) Inventors: Radovan Buffa, Humenne (SK); Ivana Basarabova, Medzilaborce (SK); Martina Hermannova, Zamberk (CZ); Katerina Knotkova, Chocen (CZ); Jaromir Kulhanek, Pardubice (CZ); Josef Chmelar, Hylvaty (CZ); Tomáš Pitucha, Chrudim (CZ); Drahomira Chladkova, Letohrad (CZ); Helena Krejci, Svitavy (CZ); Hana Vagnerova, Dolni Cermna (CZ); Martin Sojka, Holice na Ostrove (SK); Lubos Sobotka, Malsovice (CZ); Vladimir Velebny, Zamberk (CZ)

(73) Assignee: CONTIPRO A.S., Dolni Dobrouc (CZ)

( * ) Notice: Subject to any disclaimer, the term of this patent is extended or adjusted under 35 U.S.C. 154(b) by 0 days.

This patent is subject to a terminal disclaimer.

(21) Appl. No.: 17/270,693

(22) PCT Filed: Aug. 17, 2019

(86) PCT No.: PCT/CZ2019/050034
§ 371 (c)(1),
(2) Date: Feb. 23, 2021

(87) PCT Pub. No.: WO2020/038500
PCT Pub. Date: Feb. 27, 2020

(65) Prior Publication Data
US 2021/0332161 A1    Oct. 28, 2021

(30) Foreign Application Priority Data
Aug. 23, 2018 (CZ) ................. CZ2018-426

(51) Int. Cl.
*C08B 37/08* (2006.01)
*A61P 31/04* (2006.01)
*A61K 31/728* (2006.01)
*A61L 15/28* (2006.01)
*A61L 27/20* (2006.01)

(52) U.S. Cl.
CPC ........ *C08B 37/0072* (2013.01); *A61K 31/728* (2013.01); *A61L 15/28* (2013.01); *A61L 27/20* (2013.01); *A61P 31/04* (2018.01)

(58) Field of Classification Search
CPC ... C08B 37/0072; A61K 31/728; A61P 31/04; A61L 15/28; A61L 27/20
See application file for complete search history.

(56) References Cited

FOREIGN PATENT DOCUMENTS

| WO | 2005032417 A2 | 4/2005 | |
|---|---|---|---|
| WO | WO-2008094664 A1 * | 8/2008 | ............ A61P 25/00 |
| WO | 2011069475 A2 | 6/2011 | |
| WO | 2016141903 A1 | 9/2016 | |

OTHER PUBLICATIONS

Akeel, A. et al "Chlorination and oxidation of heparin and hyaluranon . . . " Free Rad. Biol. Med., vol. 56, pp. 72-88. (Year: 2013).*

Rees, M. et al "Hypochlorite-mediated fragmentation of hyaluronan . . . " JACS, vol. 125, pp. 13719-13733. (Year: 2003).*

Hui F, Debiemme-Chouvy C. Antimicrobial N-halamine polymers and coatings: a review of their synthesis, characterization, and applications. Biomacromolecules. Mar. 11, 2013;14(3):585-601.

International Search Report and Written Opinion of the International Searching Authority, dated Nov. 18, 2019, for PCT/CZ2019050034.

* cited by examiner

*Primary Examiner* — Leigh C Maier
(74) *Attorney, Agent, or Firm* — Lorenz & Kopf LLP (57) ABSTRACT

A chlorinated derivative of hyaluronic acid or of a modified hyaluronic acid (chloramide) is provided. The chloramide has an amidic group (—NH—CO—). The hydrogen of the amidic group is substituted by a chlorine atom, according to the structural formula —NCl—CO—. The substitution degree of the hyaluronic acid or of the modified hyaluronic acid by chlorine is in an amount of from 50 to 100 %.

13 Claims, 3 Drawing Sheets

CHLORINATED DERIVATIVE OF HYALURONIC ACID, METHOD OF PREPARATION THEREOF, A COMPOSITION CONTAINING THE DERIVATIVE, AND USE THEREOF

CROSS-REFERENCE TO RELATED APPLICATIONS

This application is the National Stage of International Application No. PCT/CZ2019/050034, filed on 17 Aug. 2019, which claims priority to and all advantages of CZ Application No. PV2018-426, filed on 23 Aug. 2018, both of which are incorporated herein by reference in their entirety.

TECHNICAL FIELD

The invention relates to a derivative of hyaluronic acid, in which the majority of the hydrogen atoms in the amidic group —NH—CO— is substituted by chlorine atoms —NCl—CO—. When modified in the present manner, the polymer—hyaluronan chloramide exhibits an increased reactivity in both oxidative and reductive reactions.

BACKGROUND

The Hyaluronic Acid

Hyaluronic acid or the sodium salt thereof is a non-sulfated glycosaminoglycan constituted by two repeating units of D-glucuronic acid and N-acetyl-D-glucosamine.

wherein
R$^1$ stands for hydrogen or sodium.

The molecular weight of the native hyaluronic acid is within the range of $5 \cdot 10^4$ to $5 \cdot 10^6$ g·mol$^{-1}$. This hydrophilic polysaccharide plays a significant role in numerous biological processes, such as organization of proteoglycans, hydration, or cellular differentiation, and is known to be an essential constituent of skin, synovial joint fluid and of connective tissues. The aforesaid polymer is naturally occurring in biological systems and therefore it can be characterized as being biodegradable and biocompatible. Hence, it constitutes a suitable substrate in the field of carriers of biologically active substances for a wide range of biomedical applications.

Chemical Modifications and Forms of the Hyaluronic Acid

There are numerous known methods of chemical modification of hyaluronic acid for the purpose of adjusting the physical and biological properties of the same (Burdick J. A. and Prestwich G. D., *Adv. Mater.* 23, 41-56, 2011). In case an essential change in solubility is required in connection with a particular application, the most frequently performed procedure consists in covalent linking a hydrophobic chain to the polymeric structure utilizing a biodegradable ester bond (Kettou S. et al., PV 2009-399, Buffa R. et al., WO2010105582). When modified in the above manner, such materials can be used for the preparation of various forms, such as fibres (Scudlova J. et. al., EP2925916 A1), knitted and braided fabrics (Pitucha T. et al., CZ 306354), self-supporting films (Foglarova M. et al. PV2015-166; Foglarova M. et al., *Carbohydrate Polymers*, 144, 68-75, 2016) or nanofibrous layers (Ruzickova J. et al. PV2013-913). Another possibility are non-woven fabrics formed by bonded staple microfibres, the latter being prepared utilizing the wet spinning process in a non-stationary coagulation bath (Zapotocky V. et al., *International Journal of Biological Macromolecules*, 95, 903-909, 2017).

Oxidation with Trichloroisocyanuric Acid or with Sodium Trichloroisocyanurate

Trichloroisocyanuric acid (TCC) is often used for performing the N-chlorination of structurally simpler amides to N-chloramides (Hiegel G. A. et al., *Synthetic Communications*, 35, 2099-2105, 2005), mostly in non-aqueous solvents. Furthermore, TCC is often mentioned in combination with stable radicals, such as a piperidinyloxy-type (TEMPO), for selectively oxidizing primary hydroxyl groups in presence of water. In connection with hyaluronic acid, the use of TCC along with TEMPO in water was disclosed, for example, in the patent (Buffa R. et al., WO2011069475A3), wherein no formation of chloramides but only the oxidation of primary hydroxyl groups to an aldehyde and a carboxylic acid was observed. Hence, in case of substrates containing large amounts of both secondary and primary alcohols (polysaccharides), reactions on hydroxyl groups can be expected when TCC and analogues thereof are used. The monosodium TCC salt, which is also known as sodium dichloroisocyanurate (DCC-Na), is a less reactive but better water soluble analogue of TCC. The use of DCC-Na for oxidizing amines and amides which, however, do not contain hydroxyl groups (Sun X. et al., *Ind. Eng. Chem. Res.*, 49, 22, 2010) was disclosed. The resulting chloramines were polymerized and the final substrates were successfully tested as antibacterial, antifungal and antiviral substances in the form of a latex emulsion (Cao Z. et al., *App. Mat. Inter.* 1, 2, 494-504, 2009).

On the basis of the above outputs, it can be concluded that the use of TCC or analogues thereof for preparing N-chlorinated hyaluronan amide in water in a selective manner is not expectable due to the presupposed reaction with the hydroxy groups of hyaluronan.

Oxidation of Polysaccharides with Hypochlorous Acid or with a Hypochlorite

Hypochlorous acid and the salts thereof are often used for the oxidation of hydroxyl groups of polysaccharides, mainly in combination with piperidinyloxy radicals (TEMPO) (Bragd P. et al., WO2002/48197, Buffa R. et al., WO2011/069475A3). It can be generally said that, in a great majority of cases, no formation of the respective chloramides was observed in relation to the polysaccharides containing an amide group. The early sources do not mention any presence of hyaluronan chloramide (Green S. P. et al., *J. Rheumatology*, 17, 1670-5, 1990, Lindvall S. et al., *Chem.-Biol. Interac.* 90, 1-12, 1994, Baker M. S. et al., 461-7*Arthritis and Rheumatism*, 32, 4, 1989).

The aforesaid publications describe the examination of the process of degradation of hyaluronan caused by hypochlorous acid or by salts thereof, the latter being formed in a reaction of myeloperoxidase (MPO) with hydrogen peroxide and chlorides. There are several further publications describing the degradation of glycosaminoglycans, mainly those contained in the extracellular matrix, for the purpose of simulating inflammatory processes. The main output was to be the information concerning both the process itself and the expected in vivo presence of certain chemical structures. More recent or current sources already mention chloramides of hyaluronan.

For example, the publication (Hawkins C. L. et al., *Free Radical Biology & Medicine*, 24, 9, 1396-1410, 1998) deals with the study of the mechanism of degradation of hyaluronic acid, chondroitin sulfate and other substrates, including low-molecular ones, containing an amide group. The used oxidizing agent was HOCl/ClO⁻. The authors do not assume the existence of other forms of hyaluronan chloramide than an unstable intermediate. However, the latter has never been detected in a direct manner. The reason for that lies in its rapid homolytic or reductive cleavage, both cases resulting in the formation of radicals which further react in a way leading to the degradation of the polymer.

Another article (Parsons B. J. et al., *Biochem. J.*, 381, 175-184, 2004) describes the formation of chloramides of hyaluronan, chondroitin sulfate and other substrates utilizing MPO (myeloperoxidase enzyme), hydrogen peroxide and chlorides. The authors assume, that the respective chloramides have a certain lifetime, and provide a detailed description of the degradation of such chloramides utilizing additional agents.

Another very interesting article (Rees M. D. et al., 125, 13719-13733 *J. Am. Chem. Soc.*, 2003) describes the reactions of mono, oligo and polysaccharides containing an amide group with NaClO. The aforesaid article contains a thorough analysis of the stability of chloramides of hyaluronan as well as of chondroitin sulfate, having the modification degrees of 35% and 16%, respectively, both in the presence and in the absence of other reagents and substances, such as $Cu^{2+}$ and oxygen. It was found out that the degradation is substantially accelerated by the presence of certain metals. A rapid degradation of polymeric chloramides of hyaluronan and of chondroitin sulfate at the temperature of 50° C. was observed even in the absence of metals. The degradation was significantly slower at lower temperatures. The results of the direct observations also show that the reaction of MPO with glycosaminoglycans, which takes place in the presence of hydrogen peroxide and in the presence of a physiological amount of chlorides, generates a small amount of glycosaminoglycan chloramides. Accordingly, the authors came to the conclusion that such chloramides are also generated in vivo.

On the basis of the above outputs, it can be concluded that, despite of being known, hyaluronan chloramides having a low modification degree cannot be expected to have a sufficient stability which would make them suitable for preparing compositions for biomedical applications.

Application of N-Halogenated Polymers

This section describes the outputs that also describe selected, more specific applications of chloramines or chloramides.

The summarizing article (Hui F. et al., *Biomacromolecules*, 14, 585-601, 2013) describes the preparation, analyses and applications of various materials containing an —N-halogen bond. Nevertheless, the aforesaid summary does not mention hyaluronic acid and the description relates to chitosan that is considered to be the closest related substance from the structural viewpoint. Among possible chlorinating agents, trichloroisocyanuric acid and the less reactive analogue thereof, sodium dichloroisocyanurate, were mentioned. A general advantage of the application of the materials described above consists in the efficacy against a wide variety of microorganisms, long-term stability, regenerability, safety for humans and nature, as well as its low cost. In the majority of the described applications, N-chlorine derivatives were used wherein a relatively good stability was generally observed, mainly in cases where there is no carbon with a hydrogen (alpha hydrogen) next to the N-hal group. On the other hand, the elimination of the hydrogen halides and the subsequent formation of a multiple imine bond —NHal-CH— → —N═C— may occur when alpha halogen is present. Hyaluronic acid or chitosan do contain such alpha hydrogen which means that the substrates of this type (amino saccharides) include a structural fragment that may be problematic from the viewpoint of stability.

The preparation, analysis and testing of chlorinated chitosan was also described in the article (Cao Z. et al., *Journal of Biomedical Materials Research, Part A*, 85, 99-107, 2008). A material having the form of a film was successfully tested against the microorganisms *Staphylococcus aureus* and *Escherichia coli*. A significant suppression of the formation of biofilm by the aforesaid material was observed as well. The stability at 25° C. was also observed, wherein a significant decrease in the amount of active chlorine was detected after one-month storage period, the final amount being as low as 15% of the initial value.

An N-chlorinated polyurethane in the form of a film and prepared in a reaction with a solution of $Cl_2$ (Luo J. et al., *J Bioact Compat Polym*, 30, 157-166, 2015) was successfully tested against the microorganisms *Staphylococcus aureus* (gram-positive bacteria), *Escherichia coli* (gram-negative bacteria) and *Candida albicans* (fungi). The material noticeably suppressed the growth of bacteria and, besides that, significantly inhibited the formation of biofilm.

The preparation and use of N-chloramines of a wide variety of substrates were claimed in the patent (Heller A. et al., WO 2008/094664). The substrates also included the following biopolymers: N-chlorinated chitosan, N-chlorinated polylysine and N-chlorinated deacetylated hyaluronic acid, wherein chlorine is not present on the hyaluronan amide but on its deacetylated amine. The used forms included solutions or bandages containing the respective chloramines. When applied in a topical manner, such materials provided a significant pain and itch relief. In the preparation of chloramines, numerous agents, such as HOCl, NaClO, $HClO_2$, N-chlorosuccinimide, salts of N-chlorosulfonamides, molecular chlorine, thionyl chloride, phosgene, $PCl_3$ and $PCl_5$, are mentioned.

BRIEF SUMMARY

A chlorinated derivative of hyaluronic acid or of a modified hyaluronic acid (chloramide) is provided. The chloramide has an amidic group (NH—CO—). The hydrogen of the amidic group is substituted by a chlorine atom, according to the structural formula NCl CO. The substitution degree of the hyaluronic acid or of the modified hyaluronic acid by chlorine is in an amount of from 50 to 100%.

In general, it may be stated that chloramides of hyaluronic acid having a higher modification degree (more than 50%) have not been described yet. The known chloramides only include those having a lower modification degree (not more than 35%) and, for the reasons associated with an unsatisfactory stability, neither any practical application has been described so far. But in fact, the material discussed herein would be unique in that it would simultaneously meet the following requirements:

- biological compatibility and biological degradability (occurring, e.g., in connection with particular inflammatory process in the human body)
- growth inhibition of a wide variety of microorganisms, fungi and viruses (analogously to chloramides and chloramines)
- favourable effects on healing processes (owing to the presence of hyaluronic acid)

possibility of preparing a wide range of forms (owing to the fact that the active constituent is linked to the carrying polymer by a covalent bond)

In general, the aforesaid combination is desirable in connection with both external and internal applications requiring antiviral and, simultaneously, biocompatible wound dressings, fillings, anti-adhesive barriers, membranes, pockets or wraps.

The present invention solves the preparation and use of stable, biocompatible and biodegradable compositions containing hyaluronan chloramide and exhibiting antimicrobial and antiviral effects accompanied by healing effects. Furthermore, a wide range of forms is described, which forms have largely variable surface areas, mechanical or rheological properties and degradation times.

Furthermore, the invention relates to the method of preparation of the hyaluronan chloramide, wherein the chemical modification takes place in an aqueous environment utilizing trichloroisocyanuric acid or utilizing salts of trichloroisocyanuric acid. The preparation of final composition also comprises the provision of forms containing hyaluronan chloramide. Herein, the term "form" refers to various types of materials, such as a thin film, a lyophilisate, a layer of staple fibres, an endless fibre, a woven fabric, a knitted fabric, braided fabric or a nanofibrous layer.

Furthermore, the invention relates to final compositions containing hyaluronan chloramide and to the use of such compositions in the fields where the following properties or any combinations of the following properties are required:

oxidative or reductive or antimicrobial or antifungal or antiviral activity
   biological compatibility and biological degradability
   possibility of preparing various forms having a convenient degree of stability
   possibility of controlled biodegradation rate
   possibility of controlled speed of oxidative and reductive reactions
   a significant contribution to the healing process

BRIEF DESCRIPTION OF THE DRAWINGS

Other advantages of the disclosed subject matter will be readily appreciated, as the same becomes better understood by reference to the following detailed description when considered in connection with the accompanying drawings wherein.

DETAILED DESCRIPTION

The subject matter of the present invention is a chlorinated derivative of hyaluronic acid or of a modified hyaluronic acid, also referred do as hyaluronan chloramide, in which the hydrogen of the amidic group —NH—CO— is substituted by a chlorine atom, according to the structural formula —NCl—CO—, wherein the substitution degree is 50 to 100%. Accordingly, the modified hyaluronic acid is hyaluronic acid in which some of the —OH groups are replaced by a —OCOR$^2$ group and/or some of the —CH$_2$—OH groups are replaced by a —CH=O group and/or some of the CO—OH groups are replaced by a —CO—OR$^2$ group, wherein R$^2$ is a linear or aromatic chain containing $C_1$-$C_{17}$ atoms. In various embodiments, the derivative of hyaluronic acid is selected from the group comprising ethyl ester, benzyl ester, formyl, lauroyl (C12), palmitoyl (C16), caproyl (C6), the molecular weight of the derivative, in various embodiments, ranging from 5 to 500 kg·mol$^{-1}$ and the modification degree ranging from 1 to 100%.

Furthermore, the invention relates to the method of preparation of the hyaluronan chloramide, wherein the chemical modification is realized utilizing agents containing chlorine bound to nitrogen, in various embodiments, utilizing trichloroisocyanuric acid or utilizing salts of dichloroisocyanuric acid. The method according to the invention consists particularly in that an aqueous solution of the initial hyaluronic acid or its modified derivative having the molecular weight within 40 to 2200 kg·mol$^{-1}$, is prepared, the concentration thereof being within 0.5 to 5% wt., the pH value is adjusted to the range of 2.5 to 7.5, optionally 4 to 6, e.g. utilizing acetic acid in the amount of 0.2 to 7 equivalents with respect to a hyaluronan disaccharide, and then a chlorinating agent in the amount of 0.3 to 1.5 equivalents, optionally 2-4 equivalents, with respect to a hyaluronan disaccharide is added, the mixture is left to react for 5 to 72 hours at the temperature ranging from 5 to 40° C., whereupon the resulting chloramide is isolated by precipitation. The initial substrate can be hyaluronic acid or a chemically modified derivative thereof, the molecular weight of such substrate ranging between 40 and 2200 kg·mol$^{-1}$.

The subject matter of the present invention are also compositions containing hyaluronan chloramide in which the majority of the hydrogen atoms of the amidic group is substituted by chlorine atoms and which therefore exhibits an increased reactivity in both oxidative and reductive reactions. The final compositions may also comprise modified hyaluronic acid, the chemical modification being on the carboxyl and/or hydroxyl group. The composition according to the invention exhibits antimicrobial, antifungal and antiviral activities. The concentration of chloramide contained in the composition ranges from 10 to 99% by weight and the composition further contains an additive selected from the group comprising water, sodium chloride, calcium chloride, glycerol, hyaluronic acid, chondroitin sulfate, sodium alginate, oxy-cellulose, carboxymethyl cellulose, hydroxyethyl cellulose or modified hyaluronic acid, in which some of the —OH groups are replaced by a group OCOR$^2$ and/or some of the —CH$_2$—OH groups are replaced by a group CH=O and/or some of the CO—OH groups are replaced by a —CO—OR$^2$ group, wherein R$^2$ is a linear or aromatic chain containing $C_1$-$C_{17}$ atoms. The composition can, for example, assume the form of a solution or a gel in an aqueous solution, wherein the content of the hyaluronan chloramide in the final composition, calculated in terms of the dry matter, is within the range from 10 to 100%. The composition can also assume the form of a solid substrate selected from the group comprising a self-supporting film, lyophilisate, a layer of staple fibres (a non-woven fabric), an endless fibre, a woven fabric, knitted fabric, braided fabric or a layer of nanofibres, wherein the content of the hyaluronan chloramide in the final composition, calculated in terms of the dry matter, is within the range of 10 to 100%.

The chlorinated derivative according to the invention, as well as the composition according to the invention is usable for the preparation of wound dressing or for the preparation of implantable medical devices. Non-limiting examples of such applications include products for prevention of adhesion after performing anastomoses, or products for prevention of dehiscences, or, in combination with other substances, products for surgical corrections of abdominal wall defects, or as a part of the composition of implantable wrappers for medical devices.

The preparation of final compositions further comprises the provision of the following forms containing hyaluronan chloramide:

solid forms, such as self-supporting films, lyophilisates, layers of staple fibres (non-woven fabrics), endless fibres, woven fabrics, knitted fabrics, braided fabrics or a layers of nanofibres, all of them optionally containing further additives, liquid forms, especially aqueous chloramide solutions, optionally containing further additives.

Non-limiting examples of such additives are as follows: polyethylene oxide, hyaluronic acid, chondroitin sulfate, modified hyaluronic acid in the form of esters, modified hyaluronic acid in the form of aldehydes, sodium alginate, oxy-cellulose, carboxymethyl cellulose, hydroxyethyl cellulose, esters of fatty acids, sodium chloride, potassium chloride, or calcium chloride.

Furthermore, the invention relates to the use of such compositions, particularly in the fields where the following properties or any combinations of the following properties are required:

oxidative or reductive or antimicrobial or antifungal or antiviral activity biological compatibility and biodegradability possibility of preparing various forms having a convenient degree of stability possibility of controlled biodegradation rate possibility of controlled speed of oxidative and reductive reactions a significant contribution to a healing process Stable liquid compositions on the basis of hyaluronan chloramide should not contain any additives reacting with hyaluronan chloramide. This particularly applies to the compounds, which are sensitive to oxidation (in which case, hyaluronan chloramide is subject to reduction and acts as an oxidant), and/or to strong oxidizing agents, such as those containing oxygen radicals (in which case, hyaluronan chloramide is subject to oxidation and acts as a reducing agent). For stable, solid compositions, the hyaluronan chloramide can be also combined with additives reacting therewith. Nevertheless, only those cases are applicable where the solution of hyaluronan chloramide and the additive solution cannot come into contact during the process of preparation.

A controlled biodegradation rate of the final composition can be achieved either by combining the hyaluronan chloramide with additives exhibiting a slower degradability, such as sodium alginate, carboxymethyl cellulose or chemically modified hyaluronic acid, and/or by cross-linking the hyaluronan chloramide itself utilizing, for example, polyvalent $Ca^{2+}$ cations.

A controlled rate of release of an oxidizing component can be achieved by modifying the physical properties, such as swelling, of the final composition, particularly by an addition of further, less polar additives. A non-limiting example of a less polar additive is represented by a chemically modified derivative of hyaluronic acid, said derivative having some —OH groups substituted by the —O—CO—$R^2$ group and/or —CO—OH groups substituted by the —CO—$OR^2$ group, wherein $R^2$ is a linear or aromatic chain containing $C_1$-$C_{17}$ atoms.

The final composition is usable in biomedical applications, particularly for the preparation of wound dressings, preparations against acne, antibacterial fillings, antiadhesive barriers, membranes, pockets or wrappings.

The present invention relates to the preparation and use of stable, biocompatible and biodegradable compositions containing hyaluronan chloramide, exhibiting antimicrobial and antiviral effects accompanied by healing effects. The stability of the material is described in Example 16. Furthermore, a wide range of forms is described, which forms have a large variability of surface areas, of mechanical or rheological properties and of degradation time.

The practical implementation of the technical solution according to the present invention is not complicated from the technological viewpoint and does not require any less available chemicals, solvents or isolation procedures to be used.

Figure 1A:
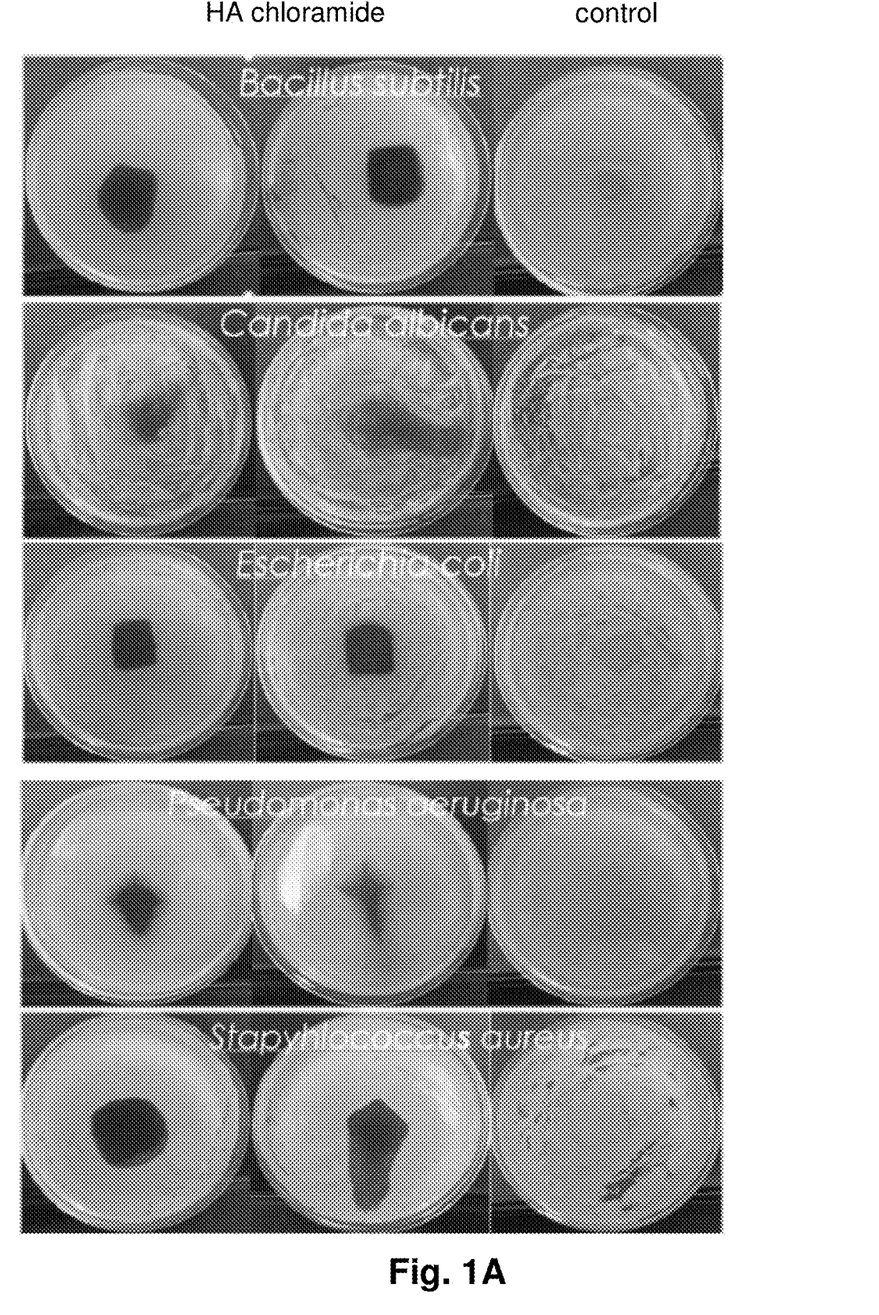
FIG. 1A is a chart illustrating antimicrobial activity of the composition assuming the form of a lyophilisate on the basis of hyaluronan chloramide as prepared according to Example 25.
Figure 1B:
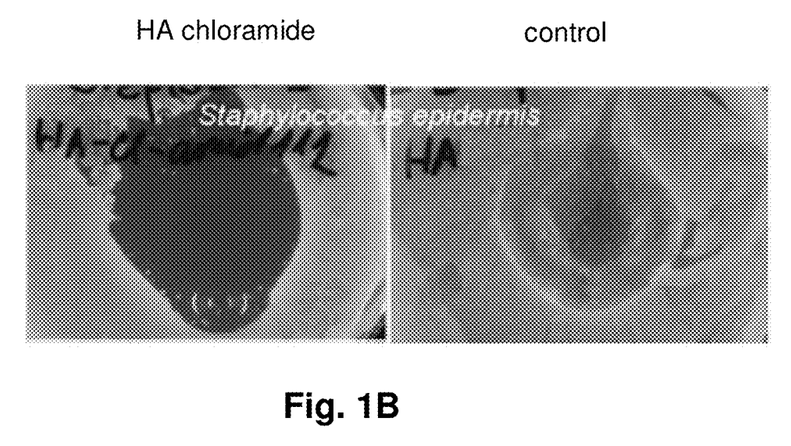
FIG. 1B is a chart illustrating antimicrobial activity of the composition assuming the form of a lyophilisate on the basis of hyaluronan chloramide as prepared according to Example 25.

The figures show the growth inhibition of the microorganisms *Bacillus subtilis, Escherichia coli, Staphylococcus aureus, Candida Albicans, Pseudomona aeruginosa, Staphylolococus* epidermis under the presence of soluble lyophilisates on the basis of hyaluronan chloramide as prepared according to Example 25 (FIG. 1A) compared to the control material, namely to the lyophilized native hyaluronic acid (FIG. 1B). The procedure of determining the antimicrobial activity is described in Example 43.

Figure 2:
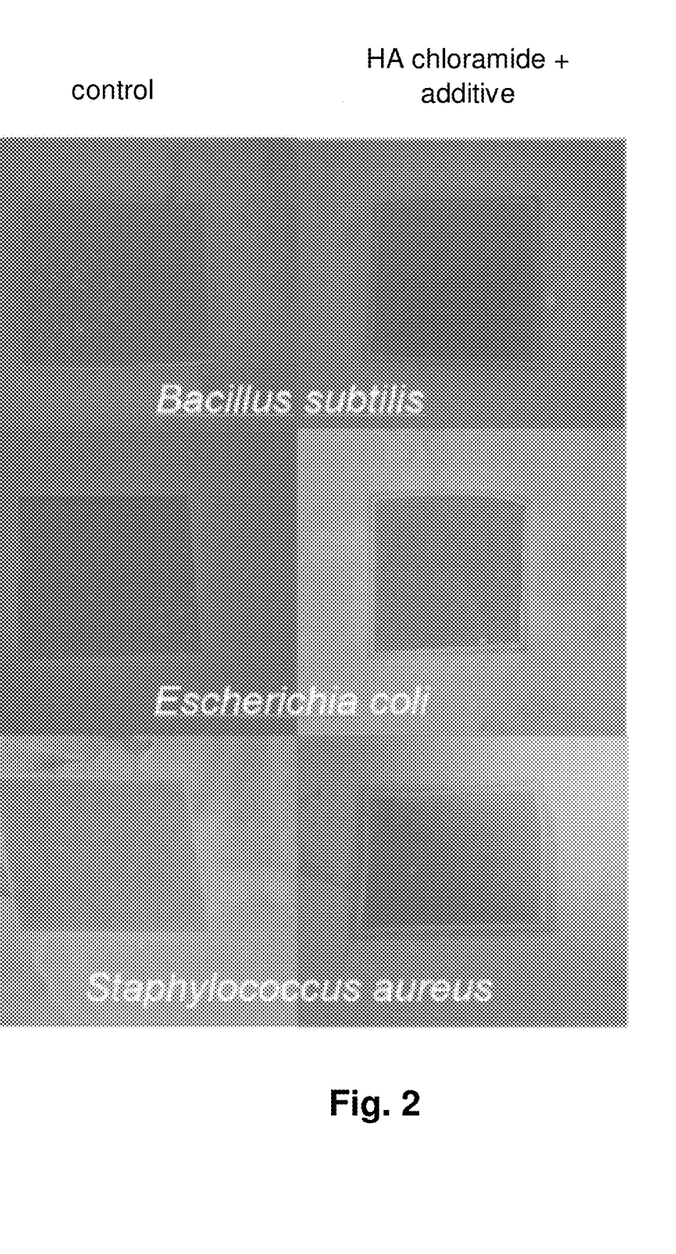
FIG. 2 is a chart illustrating antimicrobial activity of the composition assuming the form of a film on the basis of hyaluronan chloramide as prepared according to Example 32.

The figures show the growth inhibition of the microorganisms *Bacillus subtilis, Escherichia coli* and *Staphylococcus aureus* under the presence of an insoluble film on the basis of hyaluronan chloramide containing an additive constituted by hyaluronan esterified by lauric acid, the film having been prepared according to Example 32, compared to the control material prepared according to Example 31. The procedure of determining the antimicrobial activity is described in Example 43.

EXAMPLES

DS=degree of substitution=100%*(the molar amount of modified polymer units)/(the total molar amount of all polymer units)

Unless otherwise specified, the expression "equivalent" (eq) as used herein refers to a repeating unit of the respective polysaccharide, such as a hyaluronan disaccharide. Unless otherwise specified, percentages are weight percents.

As used herein, the molecular weight of polymers refers to a weight average value determined utilizing the SEC-MALLS method.

Example 1

Preparation of an Ethyl Ester of Hyaluronan

NaOH was added to an aqueous hyaluronan solution (1 g, 300 kg·mol$^{-1}$, in 40 ml of water) until reaching the pH value of 9. Subsequently, 20 ml of dimethyl sulfoxide and 0.08 ml of ethyl iodide were added and the resulting mixture was stirred at the temperature of 45° C. for 3 days. Afterwards, the resulting mixture was precipitated by 140 ml of 100% isopropanol and the solid matter separated by filtration was washed with isopropanol and vacuum dried. The product (897 mg) was analysed utilizing NMR.

The DS value of the ester was 6% (determined utilizing NMR, lit. Kettou S. et al., CZ PV 2009-399).

Example 2

Preparation of a Benzyl Ester of Hyaluronan

NaOH was added to an aqueous hyaluronan solution (1 g, 300 kg·mol$^{-1}$, in 40 ml of water) until reaching the pH value of 9. Subsequently, 20 ml of dimethyl sulfoxide and 0.08 ml of benzyl bromide were added and the resulting mixture was stirred at the temperature of 20° C. for 4 days. Afterwards, the resulting mixture was precipitated by 140 ml of 100% isopropanol and the solid matter separated by filtration was washed with isopropanol and vacuum dried. The final product (obtained in the amount of 920 mg) was analysed utilizing NMR.

The DS value of the ester was 3% (determined utilizing NMR, lit. Kettou et al., PV 2009-399).

Example 3

Preparation of an Lauroyl of Hyaluronan 70 ml of tetrahydrofuran, 4 equivalents of triethylamine and 0.1 equivalents of 4-dimethylaminopyridine were added to the solution of hyaluronan (5 g, 250 kg·mol$^{-1}$) in 100 ml of distilled water. Simultaneously, lauric acid (4 equivalents) was dissolved in the mixture of 30 ml of tetrahydrofuran and 7 ml of triethylamine and the obtained solution was supplemented with 4.8 ml of ethyl chloroformate for 15 minutes at 0 to 5° C. Subsequently, the resulting suspension was filtered into the solution of hyaluronan and the reaction mixture was stirred at 20° C. for 5 hours. The resulting solution was precipitated by adding 400 ml of 100% isopropanol and washed with 80% isopropanol and then with 100% isopropanol. Afterwards, the precipitate was dried at 40° C. for 2 days. The substitution degree was determined as 37% utilizing NMR Example 4

Preparation of a Formyl of Hyaluronan

A one-percent aqueous solution of HA (1 g, 200 kg·mol$^{-1}$) containing NaCl 1%, KBr 1%, N-acetylamino-TEMPO (0.01 eq.) and NaHCO$_3$ (20 eq.) was gradually supplemented with an aqueous solution of NaClO (0.5 eq.) under nitrogen atmosphere. The mixture was stirred at 10° C. for 12 hours whereupon 0.1 g of ethanol were added. Subsequently, the final mixture was stirred for another 1 hour. The resulting solution was diluted with distilled water to the concentration of 0.2% and dialysed against the mixture (0.1% NaCl, 0.1% NaHCO$_3$) 3 times 5 litres (1× a day) and then against distilled water 7 times 5 litres (2× a day). The final solution was evaporated and analysed.

DS 9% (determined from NMR).

Example 5

Preparation of a Hyaluronan Chloramide 5 g of hyaluronan (Mw 2200 kg·mol$^{-1}$) were dissolved in 250 ml of distilled water. Subsequently, 2 ml of acetic acid were added and the solution was stirred at the temperature of 20° C. for 15 minutes. Then, a sodium salt of dichloroisocyanuric acid in the amount of 3.2 g (1 eq.) was added. Then, the mixture was stirred at a temperature of 20° C. for 24 hours. Subsequently, the mixture was precipitated by 2.5 litres of isopropanol and filtered. The solid portion was washed with 2 litres of isopropanol, whereupon it was vacuum dried for 20 hours. DS 82% (determined by NMR).

Example 6

Preparation of a Hyaluronan Chloramide 5 g of hyaluronan (Mw 40 kg·mol$^{-1}$) were dissolved in 100 ml of distilled water. Subsequently, 2 ml of acetic acid were added and the solution was stirred at the temperature of 20° C. for 15 minutes. Then, a sodium salt of dichloroisocyanuric acid in the amount of 3.2 g (1 eq.) was added. Then, the mixture was stirred at a temperature of 20° C. for 24 hours. Subsequently, the mixture was precipitated by 2.5 litres of isopropanol and filtered. The solid portion was washed with 2 litres of isopropanol, whereupon it was vacuum dried for 20 hours. DS 83% (determined from NMR).

Example 7

Preparation of a Hyaluronan Chloramide 5 g of hyaluronan (Mw 2200 kg·mol$^{-1}$) were dissolved in 1000 ml of distilled water. Subsequently, 2 ml of acetic acid were added and the solution was stirred at the temperature of 20° C. for 15 minutes. Then, a sodium salt of dichloroisocyanuric acid in the amount of 3.2 g (1 eq.) was added. Then, the mixture was stirred at a temperature of 20° C. for 24 hours. Subsequently, the mixture was precipitated by 2.5 litres of isopropanol and filtered. The solid portion was washed with 2 litres of isopropanol, whereupon it was vacuum dried for 20 hours. DS 72% (determined from NMR).

Example 8

Preparation of a Hyaluronan Chloramide 5 g of hyaluronan (Mw 2200 kg·mol$^{-1}$) were dissolved in 250 ml of distilled water. Subsequently, 0.14 ml of acetic acid (0.2 eq.) were added and the solution was stirred at the temperature of 20° C. for 15 minutes. Then, a sodium salt of dichloroisocyanuric acid in the amount of 3.2 g (1 eq.) was added. Then, the mixture was stirred at a temperature of 20° C. for 24 hours. Subsequently, the mixture was precipitated by 2.5 litres of isopropanol and filtered. The solid portion was washed with 2 litres of isopropanol, whereupon it was vacuum dried for 20 hours. DS 53% (determined from NMR).

Example 9

Preparation of a Hyaluronan Chloramide 5 g of hyaluronan (Mw 180 kg·mol$^{-1}$) were dissolved in 250 ml of distilled water. Subsequently, 3 ml of acetic acid were added and the solution was stirred at the temperature of 20° C. for 15 minutes. Then, a sodium salt of dichloroisocyanuric acid in the amount of 3.2 g (1 eq.) was added. Then, the mixture was stirred at a temperature of 20° C. for 24 hours. Subsequently, the mixture was precipitated by 2.5 litres of isopropanol and filtered. The solid portion was washed with 2 litres of isopropanol, whereupon it was vacuum dried for 20 hours. DS 83% (determined from NMR).

Example 10

Preparation of a Hyaluronan Chloramide 5 g of hyaluronan (Mw 2200 kg·mol$^{-1}$) were dissolved in 250 ml of distilled water. Subsequently, 5 ml of acetic acid (7 eq.) were added and the solution was stirred at the temperature of 20° C. for 15 minutes. Then, a sodium salt of dichloroisocyanuric acid in the amount of 3.2 g (1 eq.) was added. Then, the mixture was stirred at a temperature of 20° C. for 24 hours. Subsequently, the mixture was precipitated by 2.5 litres of isopropanol and filtered. The solid portion was washed with 2 litres of isopropanol, whereupon it was vacuum dried for 20 hours. DS 95% (determined from NMR).

Example 11

Preparation of a Hyaluronan Chloramide 5 g of hyaluronan (Mw 2200 kg·mol$^{-1}$) were dissolved in 250 ml of distilled water. Subsequently, 2 ml of acetic acid were added and the solution was stirred at the temperature of 20° C. for 15 minutes. Then, a sodium salt of dichloroisocyanuric acid in the amount of 1.07 g (0.33 eq.) was added. Then, the mixture was stirred at a temperature of 20° C. for 24 hours. Subsequently, the mixture was precipitated by 2.5 litres of isopropanol and filtered. The solid portion was washed with 2 litres of isopropanol, whereupon it was vacuum dried for 20 hours. DS 51% (determined from NMR).

Example 12

Preparation of a Hyaluronan Chloramide 5 g of hyaluronan (Mw 2200 kg·mol$^{-1}$) were dissolved in 250 ml of distilled water. Subsequently, 2 ml of acetic acid were added and the solution was stirred at the temperature of 20° C. for 15 minutes. Then, a sodium salt of dichloroisocyanuric acid in the amount of 4.8 g (1.5 eq.) was added. Then, the mixture was stirred at a temperature of 20° C. for 24 hours. Subsequently, the mixture was precipitated by 2.5 litres of isopropanol and filtered. The solid portion was washed with 2 litres of isopropanol, whereupon it was vacuum dried for 20 hours. DS 96% (determined from NMR).

Example 13

Preparation of a Hyaluronan Chloramide 5 g of hyaluronan (Mw 2200 kg·mol$^{-1}$) were dissolved in 250 ml of distilled water. Subsequently, 2 ml of acetic acid were added and the solution was stirred at the temperature of 20° C. for 15 minutes. Then, trichloroisocyanuric acid in the amount of 2.91 g (1 eq.) was added. Then, the mixture was stirred at a temperature of 20° C. for 24 hours. Subsequently, the mixture was precipitated by 2.5 litres of isopropanol and filtered. The solid portion was washed with 2 litres of isopropanol, whereupon it was vacuum dried for 20 hours. DS 97% (determined from NMR).

Example 14

Preparation of a Hyaluronan Chloramide 5 g of hyaluronan (Mw 2200 kg·mol$^{-1}$) were dissolved in 250 ml of distilled water. Subsequently, 2 ml of acetic acid were added and the solution was stirred at the temperature of 20° C. for 15 minutes. Then, trichloroisocyanuric acid in the amount of 0.87 g (0.3 eq.) was added. Then, the mixture was stirred at a temperature of 20° C. for 24 hours. Subsequently, the mixture was precipitated by 2.5 litres of isopropanol and filtered. The solid portion was washed with 2 litres of isopropanol, whereupon it was vacuum dried for 20 hours. DS 71% (determined from NMR).

Example 15

Preparation of a Hyaluronan Chloramide 5 g of hyaluronan (Mw 2200 kg·mol$^{-1}$) were dissolved in 250 ml of distilled water. Subsequently, 2 ml of acetic acid were added and the solution was stirred at the temperature of 20° C. for 15 minutes. Then, a sodium salt of dichloroisocyanuric acid in the amount of 3.2 g (1 eq.) was added. Then, the mixture was stirred at a temperature of 20° C. for 5 hours. Subsequently, the mixture was precipitated by 2.5 litres of isopropanol and filtered. The solid portion was washed with 2 litres of isopropanol, whereupon it was vacuum dried for 20 hours. DS 52% (determined from NMR).

Example 16

Preparation of a Hyaluronan Chloramide 5 g of hyaluronan (Mw 2200 kg·mol$^{-1}$) were dissolved in 250 ml of distilled water. Subsequently, 2 ml of acetic acid were added and the solution was stirred at the temperature of 20° C. for 15 minutes. Then, a sodium salt of dichloroisocyanuric acid in the amount of 3.2 g (1 eq.) was added. Then, the mixture was stirred at a temperature of 20° C. for 48 hours. Subsequently, the mixture was precipitated by 2.5 litres of isopropanol and filtered. The solid portion was washed with 2 litres of isopropanol, whereupon it was vacuum dried for 20 hours. DS 85% (determined from NMR). The NMR solution (7 mg of the product in 0.7 ml of $D_2O$) was measured after another 5 days of standing at 20° C. The DS value was determined as 84%. The solid portion in the form of powder was let stand at 20° C. for 100 days and after that the sample was dissolved in $D_2O$. The DS value was determined as 84%.

Example 17

Preparation of a Hyaluronan Chloramide 5 g of hyaluronan (Mw 2200 kg·mol$^{-1}$) were dissolved in 250 ml of distilled water. Subsequently, 2 ml of acetic acid were added and the solution was stirred at the temperature of 20° C. for 15 minutes. Then, a sodium salt of dichloroisocyanuric acid in the amount of 3.2 g (1 eq.) was added. Then, the mixture was stirred at a temperature of 5° C. for 72 hours. Subsequently, the mixture was precipitated by 2.5 litres of isopropanol and filtered. The solid portion was washed with 2 litres of isopropanol and vacuum dried for 20 hours. DS 64% (determined from NMR).

Example 18

Preparation of a Hyaluronan Chloramide 5 g of hyaluronan (Mw 2200 kg·mol$^{-1}$) were dissolved in 250 ml of distilled water. Subsequently, 2 ml of acetic acid were added and the solution was stirred at the temperature of 20° C. for 15 minutes. Then, a sodium salt of dichloroisocyanuric acid in the amount of 3.2 g (1 eq.) was added. Then, the mixture was stirred at a temperature of 40° C. for 5 hours. Subsequently, the mixture was precipitated by 2.5 litres of isopropanol and filtered. The solid portion was washed with 2 litres of isopropanol and vacuum dried for 20 hours. DS 75% (determined from NMR).

Example 19

Preparation of a Hyaluronan Chloramide 5 g of hyaluronan (Mw 300 kg·mol$^{-1}$) were dissolved in 250 ml of distilled water. Subsequently, 2 ml of acetic acid were added and the solution was stirred at the temperature of 20° C. for 15 minutes. Then, a sodium salt of dichloroisocyanuric acid in the amount of 2.56 g (0.8 eq.) was added. Then, the mixture was stirred at a temperature of 20° C. for 24 hours. Subsequently, the mixture was precipitated by 2.5 litres of isopropanol and filtered. The solid portion was washed with 2 litres of isopropanol and vacuum dried for 20 hours. DS 79% (determined from NMR).

Example 20

Preparation of a Hyaluronan Chloramide 5 g of hyaluronan (Mw 300 kg·mol$^{-1}$) were dissolved in 350 ml of distilled water. Subsequently, 2 ml of acetic acid were added and the solution was stirred at the temperature of 20° C. for 5 minutes. Then, a sodium salt of dichloroisocyanuric acid in the amount of 2.56 g (0.8 eq.) was added. Then, the mixture was stirred at a temperature of 17° C. for 22 hours. Subsequently, the mixture was precipitated by 2.5 litres of isopropanol and filtered. The solid portion was washed with 2 litres of isopropanol and vacuum dried for 20 hours. DS 66% (determined from NMR).

Example 21

Preparation of a Hyaluronan Chloramide 5 g of hyaluronan (Mw 300 kg·mol$^{-1}$) were dissolved in 250 ml of distilled water. Subsequently, 2 ml of acetic acid were added and the solution was stirred at the temperature of 5° C. for 15 minutes. Then, a sodium salt of dichloroisocyanuric acid in the amount of 2.56 g (0.8 eq.) was added. Then, the mixture was stirred at a temperature of 5° C. for 24 hours. Subsequently, the mixture was precipitated by 2.5 litres of isopropanol and filtered. The solid portion was washed with 2 litres of isopropanol, whereupon it was vacuum dried for 20 hours. DS 50% (determined from NMR).

Example 22

Preparation of Chloramide of an Ethyl Ester of Hyaluronan 0.5 g of ethyl ester of hyaluronan prepared according to Example 1 were dissolved in 25 ml of distilled water. Subsequently, 0.2 ml of acetic acid were added and the solution was stirred at the temperature of 20° C. for 15 minutes. Then, a sodium salt of dichloroisocyanuric acid in the amount of 0.32 g (1 eq.) was added. Then, the mixture was stirred at a temperature of 20° C. for 24 hours. Subsequently, the mixture was precipitated by 250 ml of isopropanol and filtered. The solid portion was washed with 0.2 litres of isopropanol and vacuum dried for 20 hours. DS 80% (determined from NMR).

Example 23

Preparation of Chloramide of an Benzyl Ester of Hyaluronan 0.5 g of benzyl ester of hyaluronan prepared according to Example 2 were dissolved in 25 ml of distilled water. Subsequently, 0.2 ml of acetic acid were added and the solution was stirred at the temperature of 20° C. for 15 minutes. Then, a sodium salt of dichloroisocyanuric acid in the amount of 0.32 g (1 eq.) was added. Then, the mixture was stirred at a temperature of 20° C. for 24 hours. Subsequently, the mixture was precipitated by 0.25 litres of isopropanol and filtered. The solid portion was washed with 0.2 litres of isopropanol, whereupon it was vacuum dried for 20 hours. DS 78% (determined from NMR).

Example 24

Preparation of a Formyl of Hyaluronan 0.5 g of formyl of hyaluronan prepared according to Example 4 were dissolved in 25 ml of distilled water. Subsequently, 0.2 ml of acetic acid were added and the solution was stirred at the temperature of 20° C. for 15 minutes. Then, a sodium salt of dichloroisocyanuric acid in the amount of 0.32 g (1 eq.) was added. Then, the mixture was stirred at a temperature of 20° C. for 24 hours. Subsequently, the mixture was precipitated by 0.25 litres of isopropanol and filtered. The solid portion was washed with 0.2 litres of isopropanol and vacuum dried for 20 hours. DS 75% (determined from NMR).

Example 25

Preparation of a Lyophilized Hyaluronan Chloramide

A solution of 0.2 g of the hyaluronan chloramide prepared according to Example 5 in 10 ml of distilled water was, immediately following the homogenization, deep frozen at the temperature of −50° C. and lyophilized. The DS value was determined as 70% utilizing NMR.

Example 26

Preparation of a Lyophilized Chloramide of an Ethyl Ester of Hyaluronan

A solution of 0.2 g of the chloramide of ethyl ester of hyaluronan prepared according to Example 22 in 10 ml of distilled water was, immediately following the homogenization, deep frozen at the temperature of −50° C. and lyophilized. The DS value was determined as 68% utilizing NMR.

Example 27

Preparation of a Lyophilized Chloramide of an Benzyl Ester of Hyaluronan

A solution of 0.2 g of the chloramide of benzyl ester of hyaluronan prepared according to Example 23 in 10 ml of distilled water was, immediately following the homogenization, deep frozen at the temperature of −50° C. and lyophilized. The DS value was determined as 67% utilizing NMR.

Example 28

Preparation of a Non-Woven Fabric from Staple Fibres Made of Hyaluronan Chloramide For the preparation of a 2% solution hyaluronan chloramide (Example 14) was used, having the substitution degree of 71% according to NMR. The above constituent was weighed and supplemented with the required amount of distilled water. The whole mixture was stirred in a mixer at room temperature, the set speed of the latter being 500 rpm and the stirring time being 24 hours. The final solution was clear and slightly viscous. The method of preparation of staple fibres is based on the precipitation of a polymer solution in a stream of a mobile coagulation bath containing 100% isopropanol. Subsequently, the solution was dosed at room temperature through extrusion nozzles into a stream of a coagulation bath fed through spinning tubes (1 tube/8 mm diameter), the controlled flow rate of the bath being 1.15 m/s. The formation of staple fibres was obtained utilizing precipitation. The formed fibres were wafted in the bath stream, caught by separation combs and transferred into the maturation bath containing 100% isopropanol. Immediately after entering the maturation bath, the raw fibres were ground up by rotating blades of a mixer, the ratio between the amount of the fibres and that of the bath being 0.5 g/350 nil. The final fibrous dispersion was filtered through a porous substrate through a filter frame. For the given experiment, a filter frame having the surface area of 64 cm² was used. After having been filtered, the fibres were transferred onto a drying device utilizing a PAD knitted fabric, with the fixation of the non-woven fabric. Prior to being placed onto the drying device, the fibres were freed from the precipitant residues utilizing a roller. The non-woven fabric was dried at the temperature of 40° C. for 30 minutes. The resulting layer was separated from the substrate as a self-supporting layer and weighed utilizing an analytic balance. The areal weight of the fabric was 50.2 g/m². The substitution degree of the formed non-woven fabric was determined as 64% utilizing NMR.

Example 29

Preparation of a Nanofibrous Layer from Hyaluronan Chloramide

For the preparation of a nanofibrous layer containing hyaluronic acid, an aqueous solution having the following composition was prepared. The concentration of the hyaluronan chloramide, which had been prepared according to Example 5, in the dry matter was 37.5%, the concentration of the native hyaluronan having the molecular weight of 80 kg·mol$^{-1}$ was 37.5%, and the amount of polyethylene oxide having the molecular weight of 600 kg·mol$^{-1}$ was 25%. The overall concentration of the dry matter was 5%. The solution was fed into a syringe and spun in an electrostatic field on a plate-type collector using a needleless linear nozzle, the voltage and spacing between the emitter and the collector being 50 kV and 16 cm, respectively. The dimension of the fibres was 110±27 nm. The DS value was determined as 30% utilizing NMR.

Example 30

Preparation of a Self-Supporting Film from Hyaluronan Chloramide

The preparation of the film took place in a special drying device where the film was dried in a closed chamber. The apparatus was equipped with the bottom and top plates with controllable temperatures. The detailed description of the apparatus is provided in the publication Foglarova et al., PV2015-166; FoglarovaM. Et al., *Carbohydrate Polymers* 2016, 144, 68-75. The weighed amount of 200 mg of the hyaluronan chloramide described in Example 5 was dissolved in 20 ml of demineralised water whereupon the resulting solution was stirred for 2 hours. Then, the final solution was dosed into the drying device onto a pad (hydrophobized glass) and dried in a closed chamber for 18 hours. The bottom and top plates of the dryer had the temperatures of 50° C. and 20° C., respectively. After having been dried, the film was released from the pad and kept for future use. The DS value was determined as 60% utilizing NMR.

Example 31

Preparation of a Self-Supporting Film from Lauroyl Hyaluronan and Native Hyaluronan (4/1)

The preparation of the film took place in the device described in Example 30. The weighed amount of 160 mg of the lauroyl derivative of sodium hyaluronate (as described in Example 3) was dissolved in 16 ml of an aqueous solution of 2-propanol (50% w/w) whereupon the resulting solution was stirred for 18 hours. The weighed amount of 40 mg of native hyaluronan having the molecular weight of 330 kg·mol$^{-1}$ was dissolved in 4 ml of demineralised water whereupon the resulting solution was stirred for 18 hours. Subsequently, both solutions were mixed and stirred for 30 minutes. Then, the resulting mixed solution was dosed into the drying device onto a pad (hydrophobized glass) and dried in a closed chamber for 7 hours. The bottom and top plates of the dryer had the temperatures of 50° C. and 20° C., respectively. After having been dried, the film was released from the pad and kept for future use.

Example 32

Preparation of a Self-Supporting Film from Lauroyl Hyaluronan and Hyaluronan Chloramide (3/1)

The preparation of the film took place in the device described in Example 30. The weighed amount of 150 mg of the lauroyl derivative of sodium hyaluronate (as described in Example 3) was dissolved in 15 ml of an aqueous solution of 2-propanol (50% w/w) whereupon the resulting solution was stirred for 18 hours. The weighed amount of 50 mg of the hyaluronan chloramide described in Example 5 was dissolved in 5 ml of demineralised water whereupon the resulting solution was stirred for 2 hours. Subsequently, both solutions were mixed and stirred for 30 minutes. Then, the resulting mixed solution was dosed into the drying device onto a pad (hydrophobized glass) and dried in a closed chamber for 7 hours. The bottom and top plates of the dryer had the temperatures of 50° C. and 20° C., respectively. After having been dried, the film was released from the pad and kept for future use. The DS value of the hyaluronan chloramide in the final material was determined as 25% utilizing NMR.

Example 33

Preparation of a Self-Supporting Film from Lauroyl Hyaluronan and Hyaluronan Chloramide (4/1)

The preparation of the film took place in the device described in Example 30. The weighed amount of 160 mg of the lauroyl derivative of sodium hyaluronate (as described in Example 3) was dissolved in 16 ml of an aqueous solution of 2-propanol (50% w/w) whereupon the resulting solution was stirred for 18 hours. The weighed amount of 40 mg of the hyaluronan chloramide described in Example 5 was dissolved in 4 ml of demineralised water whereupon the resulting solution was stirred for 2 hours. Subsequently, both the solutions were mixed and stirred for 30 minutes. Then, the resulting mixed solution was dosed into the drying device onto a pad (hydrophobized glass) and dried in a closed chamber for 7 hours. The bottom and top plates of the dryer had the temperatures of 50° C. and 20° C., respectively. After having been dried, the film was released from the pad and kept for future use. The DS value of the hyaluronan chloramide in the final material was determined as 20% utilizing NMR.

Example 34

Preparation of a Knitted Fabric from Fibres Made of Hyaluronan Chloramide

The initial raw material used for the formation of the fibres was hyaluronan chloramide prepared according to Example 14. By dissolving the aforesaid polymer in demineralised water, a solution having the concentration of 4.7% was prepared. After dissolution, the solution was transferred into a syringe and degassed utilizing a centrifuge. The solution was dosed at the speed of 200 µl/min into the coagulating bath composed of a mixture of lactic acid and isopropanol, 1:4. The fibre was wound at the speed of 1.45 m/min. Subsequently, the fibre was washed with isopropyl alcohol and dried. The fibre had the following characteristics: fineness of 9 tex, tensile strength of 1.0 N and elongation of 11%. The DS value of the chloramide was determined as 34% utilizing NMR. For the purpose of obtaining a knitted fabric, three fibres were bundled and twisted in a ring-type twisting frame, the feeding rate being 10 m/min and the spindle speed being 3000 $min^{-1}$; the value of the final twist was 300 $m^{-1}$. Using a double-bed warp knitting machine, a double-faced weft knitted fabric having a closed-loop binding was manufactured from the threads. The final knitted strip had the width of 10 mm, the basis weight of 99 $g \cdot m^{-2}$ and the loop density of 36 $cm^{-2}$.

Example 35

Preparation of a Knitted Fabric from Fibres Made of Lauroyl Hyaluronan and Hyaluronan Chloramide (4/1)

The initial raw material used for the formation of the fibres was the combination comprising 400 mg of lauroyl hyaluronan prepared according to Example 3 and 100 mg of hyaluronan chloramide prepared according to Example 14. The weighed amount of hyaluronan chloramide was dissolved in 6 ml of demineralised water whereupon 5.1 ml of isopropanol and a weighed amount of lauroyl hyaluronan (DS according to NMR: 91%, MW 300-350 kDa) were added. The prepared solution, which had the concentration of 4.5%, was transferred into a syringe and degassed utilizing a centrifuge. Subsequently, the solution was dosed at the velocity of 200 µl/min into the coagulating bath composed of a mixture of lactic acid and isopropanol, 1:4. The fibre was wound at the speed of 1.32 m/min. Afterwards, the fibre was washed with isopropyl alcohol, stabilised with acetone and dried. The fibre had the following characteristics: fineness of 8 tex, tensile strength of 0.7 N and elongation of 16%. For the purpose of obtaining a knitted fabric, three fibres were bundled and twisted in a ring-type twisting frame, the feeding rate being 10 m/min and the spindle speed being 3000 $min^{-1}$; the value of the final twist was 300 $m^{-1}$. Using a double-bed warp knitting machine, a double-faced weft knitted fabric having a closed-loop binding was manufactured from the threads. The final knitted strip had the width of 10 mm, the basis weight of 91 $g \cdot m^{-2}$ and the loop density of 36 $cm^{-2}$.

Example 36

Preparation of a Lyophilizate: Oxycellulose/Hyaluronan Chloramide

A solution of 0.3 g of oxycellulose (Mw 50 $kg \cdot mol^{-1}$) and 0.1 g of the hyaluronan chloramide prepared according to Example 5 in 100 ml of distilled water was, immediately following the homogenization, deep frozen at the temperature of −50° C. and lyophilized. The DS value of the hyaluronan chloramide was determined as 24% utilizing NMR.

Example 37

Preparation of a Lyophilizate: Alginate/Hyaluronan Chloramide

A solution of 0.3 g of alginate (Mw 40 $kg \cdot mol^{-1}$) and 0.1 g of the hyaluronan chloramide prepared according to Example 5 in 100 ml of distilled water was, immediately following the homogenization, deep frozen at the temperature of −50° C. and lyophilized. The DS value of the hyaluronan chloramide was determined as 26% utilizing NMR.

Example 38

Preparation of a Lyophilizate: Carboxymethyl Cellulose/Hyaluronan Chloramide

A solution of 0.3 g of carboxymethyl cellulose (Mw 30 $kg \cdot mol^{-1}$) and 0.03 g of the hyaluronan chloramide prepared according to Example 5 in 100 ml of distilled water was, immediately following the homogenization, deep frozen at the temperature of −50° C. and lyophilized. The DS value of the hyaluronan chloramide was determined as 3% utilizing NMR.

Example 39

Preparation of a Lyophilizate: Chondroitin Sulfate/Hyaluronan Chloramide

A solution of 0.03 g of chondroitin sulfate (Mw 45 $kg \cdot mol^{-1}$) and 0.3 g of the hyaluronan chloramide prepared according to Example 5 in 100 ml of distilled water was, immediately following the homogenization, deep frozen at the temperature of −50° C. and lyophilized. The DS value of the hyaluronan chloramide was determined as 75% utilizing NMR.

Example 40

Preparation of a Lyophilizate: Hydroxyethyl Cellulose/Hyaluronan Chloramide

A solution of 0.3 g of hydroxyethyl cellulose (Mw 45 $kg \cdot mol^{-1}$) and 0.1 g of the hyaluronan chloramide prepared according to Example 5 in 100 ml of distilled water was, immediately following the homogenization, deep frozen at the temperature of −50° C. and lyophilized. The DS value of the hyaluronan chloramide was determined as 25% utilizing NMR.

Example 41

Preparation of a Lyophilizate: Hyaluronan Formyl/Hyaluronan Chloramide

A solution of 0.3 g of formyl hyaluronan (Mw 45 $kg \cdot mol^{-1}$) prepared according to Example 4 and 0.1 g of the hyaluronan chloramide prepared according to Example 5, in 100 ml of distilled water was, immediately following the homogenization, deep frozen at the temperature of −50° C. and lyophilized. The DS value of the hyaluronan chloramide was determined as 25% utilizing NMR.

Example 42

Preparation of a Lyophilizate: Hyaluronan Chloramide Cross-Linked with $CaCl_2$

A solution of hyaluronan chloramide (0.1 g) prepared according to Example 5 in 100 ml of distilled water was supplemented with 0.01 g of $CaCl_2.2H_2O$ and the mixture was stirred at 20° C. for 1 hour. Following the homogenization, the final viscous solution was deep frozen at the temperature of −50° C. and lyophilized. The DS value of the hyaluronan chloramide was determined as 64% utilizing NMR.

Example 43

In Vitro Antimicrobial Activity Testing (FIGS. 1 and 2):

For the individual microorganisms subjected to testing, suspensions having the concentration of approximately $10^5$ CFU/ml were prepared. The suspension in the amount of 100 µl was inoculated on the surface of tryptone soya agar in Petri dishes (an approximate count of microorganisms applied in each dish was $10^4$ CFU). The suspension was uniformly spread over the entire surface of the dish utilizing a sterile loop. After absorbing the suspension in agar, the surface of agar was covered by sterile square-shaped samples selected for testing. The testing bacterium strains were being cultivated at 37° C. for 24 hours. The tests involved the examination of the lyophilized hyaluronan chloramide as prepared according to Example 25 and the self-supporting films containing hyaluronan chloramide as prepared according to Example 32, the respective control materials being constituted by analogous square-shaped pieces having no content of hyaluronan chloramide. For that purpose, square pieces having a weight ranging between 8 and 12 mg and approximate dimension of 15 mm×15 mm were prepared. For efficacy testing, the diffusion plate method (2D layout) was selected. For the cultivation, a non-selective substrate (tryptone soya agar) was selected. The square-shaped samples were tested for the following microorganisms: *Bacillus subtilis, Escherichia coli, Staphylococcus aureus, Candida Albicans, Pseudomona aeruginosa, Staphylolococus epidermis*. FIGS. 1 and 2 clearly show that the compositions containing hyaluronan chloramide according to the invention provide a significantly higher efficacy of bacterial growth inhibition, compared to the control material having no content of hyaluronan chloramide.

Example 44

Testing of Antiviral Activity Based on the Plaque Reduction:

Number of repeats—5, tested substance prepared according to Example 19, virus subject to testing: CVB3 (Nancy) in the concentration of 3×10E7, 5 PFU/ml, VERO cellular substrate Procedure:

After having been subject to $10^7$-fold dilution in the volume of 1.5 ml, the virus was adsorbed on the cell substrate in Petri dishes for 30 minutes. The negative control contained PBS without viruses. Afterwards, the virus was removed by suction and the cells were interlayered by the tested substance (or by HA and PBS contained in the negative control materials), incubation at 37° C. and in the presence of 5% of $CO_2$, for 5 hours. The cells were washed with PBS and covered by a layer of a medium containing EMEM supplemented with 5% of inactivated FBS and 0.75% of agarose. The incubation in an environment containing 5% of $CO_2$ at 37° C. for 4 days. Subsequently, the medium was removed, the cells were stained by a crystal violet dye and the counts of plaques were determined. During the test, the antiviral activity was proportional to the reduction of the number of plaques.

| Description of the group | Incubation with the tested substance | PFU on PD | | | | | Average | SD |
|---|---|---|---|---|---|---|---|---|
| Examination of the cells with PBS | PBS | 0 | 0 | 0 | 0 | 0 | 0 | 0 |
| Examination of the cells with HA | 1% chloramide of HA in PBS | 0 | 0 | 0 | 0 | 0 | 0 | 0 |
| Examination of toxicity | 1% chloramide of HA in PBS | 0 | 0 | 0 | 0 | 0 | 0 | 0 |
| Examination of the virus with PBS | PBS | 13 | 9 | 7 | 14 | 10 | 10.6 | 2.88 |
| Examination of the virus with HA | 1% HA in PBS | 10 | 6 | 14 | 12 | 10 | 10.4 | 2.97 |
| Test 1 | 0.1% HA chloramide in PBS | 5 | 7 | 10 | 8 | 9 | 7.8 | 1.92 |
| Test 2 | 0.5% HA chloramide in PBS | 8 | 5 | 8 | 7 | 8 | 7.2 | 1.3 |
| Test 3 | 1% HA chloramide in PBS | 4 | 1 | 2 | 3 | 3 | 2.6 | 1.14 |

FBS—fetal bovine serum, VERO—stabilized cellular line derived from a kidney of Cercopithecus aethiops, EMEM—Eagle's minimum essential medium, 3 × 10E7.5 PFU/ml—the concentration of the virus used for preparing the infective suspension - 3 × 10E7.5 plaque-forming units per ml, where PFU/ml is the unit of quantity of the virus and PFU are plaque-forming units, PD—Petri dish, SD—standard deviation.

The obtained results clearly show that the presence of hyaluronan chloramide causes an inhibition of the viral growth (Tests 1, 2 and 3) when compared to the standard "Examination of the viruses with HA", said inhibition becoming more efficient with increasing concentration of hyaluronan chloramide.

The terms "comprising" or "comprise" are used herein in their broadest sense to mean and encompass the notions of "including," "include," "consist(ing) essentially of," and "consist(ing) of. The use of "for example," "e.g.," "such as," and "including" to list illustrative examples does not limit to only the listed examples. Thus, "for example" or "such as" means "for example, but not limited to" or "such as, but not limited to" and encompasses other similar or equivalent examples. The term "about" as used herein serves to reasonably encompass or describe minor variations in numerical values measured by instrumental analysis or as a result of sample handling. Such minor variations may be in the order of ±0-25, ±0-10, ±0-5, or ±0-2.5, % of the numerical values. Further, The term "about" applies to both numerical values when associated with a range of values. Moreover, the term "about" may apply to numerical values even when not explicitly stated.

Generally, as used herein a hyphen "-" or dash "–" in a range of values is "to" or "through"; a ">" is "above" or "greater-than"; a "≥" is "at least" or "greater-than or equal to"; a "<" is "below" or "less-than"; and a "≤" is "at most" or "less-than or equal to." On an individual basis, each of the aforementioned applications for patent, patents, and/or patent application publications, is expressly incorporated herein by reference in its entirety in one or more non-limiting embodiments.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

The present invention has been described herein in an illustrative manner, and it is to be understood that the terminology which has been used is intended to be in the nature of words of description rather than of limitation. Many modifications and variations of the present invention are possible in light of the above teachings. The present invention may be practiced otherwise than as specifically described within the scope of the appended claims. The subject matter of all combinations of independent and dependent claims, both single and multiple dependent, is herein expressly contemplated.

The invention claimed is:

1. A chlorinated derivative of hyaluronic acid or of a modified hyaluronic acid (chloramide), the chloramide having an amidic group (—NH—CO—), wherein the hydrogen of the amidic group is substituted by a chlorine atom, according to the structural formula —NCl—CO—, and wherein the substitution degree of the hyaluronic acid or of the modified hyaluronic acid by chlorine is in an amount of from 50 to 100%.

2. The chlorinated derivative according to claim 1, wherein the modified hyaluronic acid is hyaluronic acid having an —OH group, a —CH$_2$—OH, and a —CO—OH group and wherein:
(A) at least a portion of the —OH groups are substituted by a —O—CO—R$^2$ group, where R$^2$ is a C$_1$-C$_{17}$ linear or aromatic group;
(B) at least a portion of the —CH$_2$—OH groups are substituted by a CH=O group;
(C) at least a portion of the —CO—OH groups are substituted by a —CO—OR$^2$ group; where R$^2$ is a C$_1$-C$_{17}$ linear or aromatic group; or
(D) any combination of (A), (B), and (C).

3. The chlorinated derivative according to claim 2, wherein the modified hyaluronic acid is selected from the group comprising ethyl ester, benzyl ester, formyl, lauroyl (C12), palmitoyl (C16), and/or caproyl (C6) modified hyaluronic acid.

4. The chlorinated derivative according to claim 1, wherein its molecular weight is 5 to 500 kg·mol$^{-1}$.

5. A method of preparation of the chloramide of hyaluronic acid or of a modified hyaluronic acid, according to claim 1, the method comprising:
preparing an aqueous solution of the initial hyaluronic acid or its modified derivative having the molecular weight within 40 to 2200 kg·mol$^{-1}$, the concentration of the initial hyaluronic acid or its modified derivative being within 0.5 to 5% wt., based on a total weight of the aqueous solution;
adjusting the pH of the aqueous solution to the range of 2.5 to 7.5;
combining a chlorinating agent and the aqueous solution in the amount of 0.3 to 1.5 equivalents with respect to a hyaluronan disaccharide to form a mixture;
exposing the mixture for 5 to 72 hours to a temperature of from 5 to 40° C. to react; and
isolating the chloramide by precipitation.

6. The method of preparation according to claim 5, wherein the pH is adjusted to the range of 4 to 6.

7. The method of preparation according to claim 5, wherein the pH is adjusted by adding acetic acid in the amount of 0.2 to 7 equivalents with respect to the hyaluronan disaccharide.

8. The method of preparation according to claim 5, wherein the chlorinating agent is trichloroisocyanuric acid or a sodium salt of dichloroisocyanuric acid.

9. An antimicrobial, antifungal and antivirus composition, wherein the composition comprises:
the derivative according to claim 1 in a concentration of from 10 to 99% wt., based on a total weight of the composition; and
an additive selected from the group of water, sodium chloride, calcium chloride, glycerol, hyaluronic acid, chondroitin sulfate, sodium alginate, oxy-cellulose, carboxymethyl cellulose, hydroxyethyl cellulose, a modified hyaluronic acid, and combinations thereof, with the proviso that when the additive comprises a modified hyaluronic acid;
(A) at least a portion of the —OH groups of modified hyaluronic acid are substituted by a —O—CO—R$^2$ group, where R$^2$ is a C$_1$-C$_{17}$ linear or aromatic group;
(B) at least a portion of the —CH$_2$—OH groups are substituted by a —CH=O group;
(C) at least a portion of the —CO—OH groups are substituted by a —CO—OR$^2$ group, where R$^2$ is a C$_1$-C$_{17}$ linear or aromatic group; or
(D) any combination of (A), (B), and (C).

10. The composition according to claim 9, wherein the composition is in the form of a solution or a gel in an aqueous solution, wherein the content of the chloramide in the composition, calculated in terms of the dry matter, is within the range of from 10 to 100%.

11. The composition according to claim 9, wherein the composition is in the form of a solid substrate selected from the group of a self-supporting film, lyophilisate, a layer of staple fibres, an endless fibre, a woven fabric, knitted fabric, braided fabric, a layer of nanofibers, and combinations thereof, and wherein the content of the chloramide in the composition, calculated in terms of the dry matter, is within the range of from 10 to 100%.

12. The chlorinated derivative according to claim 1, utilized for the preparation of wound covers or for the preparation of implantable medical devices.

13. The composition according to claim 9, utilized for the preparation of wound covers or for the preparation of implantable medical devices.

* * * * *